United States Patent [19]
Jonson et al.

[11] Patent Number: 5,400,778
[45] Date of Patent: Mar. 28, 1995

[54] METHOD AND DEVICE FOR REDUCTION OF REBREATHING OF GAS FROM DEAD SPACE

[75] Inventors: Björn Jonson, Lund; Sven-Gunnar Olsson, Arlöv, both of Sweden

[73] Assignee: Siemens-Elema AB, Solna, Sweden

[21] Appl. No.: 955,872

[22] PCT Filed: Jun. 18, 1991

[86] PCT No.: PCT/SE91/00435

§ 371 Date: Dec. 10, 1992

§ 102(e) Date: Dec. 10, 1992

[87] PCT Pub. No.: WO91/19526

PCT Pub. Date: Dec. 26, 1991

[30] Foreign Application Priority Data

Jun. 18, 1990 [SE] Sweden .................. 9002161

[51] Int. Cl.⁶ .................. A62B 7/00; A61M 16/00; F16K 31/02
[52] U.S. Cl. .................. 128/205.19; 128/207.14; 128/204.23
[58] Field of Search .................. 128/205.12, 204.25, 128/204.26, 205.19, 205.24, 207.14–207.16, 911, 912, 204.21, 204.23

[56] References Cited

U.S. PATENT DOCUMENTS

| | | | |
|---|---|---|---|
| 3,794,026 | 2/1974 | Jacobs | 128/204.26 |
| 4,206,754 | 6/1980 | Cox et al. | 128/204.23 |
| 4,265,237 | 5/1981 | Schwanbom et al. | 128/207.14 |
| 4,270,530 | 6/1981 | Baum et al. | 128/207.14 |
| 4,519,388 | 5/1985 | Schwanbom et al. | 128/204.25 |
| 4,565,194 | 1/1986 | Weerda et al. | 128/205.19 |
| 4,573,462 | 3/1986 | Baum | 128/207.15 |
| 4,596,247 | 6/1986 | Whitwam et al. | 128/204.25 |
| 4,646,733 | 3/1987 | Stroh et al. | 128/207.16 |
| 5,186,167 | 2/1993 | Kolobow | 128/207.14 |
| 5,291,882 | 3/1994 | Makhoul et al. | 128/200.26 |

FOREIGN PATENT DOCUMENTS 3204110 8/1984 Germany .................. 128/205.19

OTHER PUBLICATIONS

Derwent's Abstract No. A56 27 K/02, SU 908-371, Feb. 28, 1982.

Primary Examiner—Kimberly L. Asher
Attorney, Agent, or Firm—Hill, Steadman & Simpson

[57] ABSTRACT

In a method and apparatus for reducing rebreathing of gas from the dead space (i.e., the volume of used gas, which during expiration has filled the airways and is brought back to the alveus at the following inspiration), at least during the final phase of expiration, a flow of used breathing gas is artificially evacuated from the patient through a gas conduit inserted into the patient's airway, the flow rate of evacuated gas being greater than the flow rate of the expiration gas which is being exhaled by the patient at the time. A flow of breathable gas is simultaneously supplied to the patient through gas conduit inserted in the airway, which may be the same conduit as is used for evacuation or a different conduit.

7 Claims, 2 Drawing Sheets

METHOD AND DEVICE FOR REDUCTION OF REBREATHING OF GAS FROM DEAD SPACE

BACKGROUND OF THE INVENTION

1. Field of the Invention

The present invention relates to a method for reduction of rebreathing of gas from dead space and a device for practicing the method. Dead space means the volume of used gas, which during the expiration has filled the airways and is brought back to the alveolus at the following inspiration.

2. Description of the Prior Art

Several diseases result in difficulties or makes it impossible for the patient to achieve sufficient ventilation for adequate gas exchange of the alveolar space in the lungs. This results in the blood, which leaves the lungs, not having appropriate content of oxygen and carbon dioxide which often is referred to as respiratory insufficiency. Lack of oxygen can usually be rectified by supplying to the patient breathing gas having a higher oxygen content than that present in air, but for carbon dioxide a positive effect cannot be achieved in a corresponding way. At serious respiratory insufficiency, respiratory treatment is applied to ensure the patient a sufficient alveolar ventilation. However, if the function of the lungs is seriously disturbed respiratory treatment can result in the pressure in the airway during injection of the breathing volume being very high, which can then present a risk that the airway and the lung tissue are further damaged, a phenomenon often called barotrauma. In order to reduce the requirements of ventilation drastic actions are taken such as narcosis and muscle relaxation, reduction of the body temperature and extracorporeal elimination of carbon dioxide, but such measurements are extremely resource demanding and of limited medical utility.

Positive pressures in the airway also result in other disadvantages except barotrauma: at circulation disturbances the circulation is often retarded in a detrimental way by positive intrapulmonal pressures. In such cases it is important to try to reduce the positive pressure and a method for achieving this is to decrease the volumes by which a patient is ventilated in a respirator.

A well-known principle for treatment of respiratory insufficiency is to decrease the dead space, and this can be achieved by the patient being tracheotomied, which means that on the throat a ventilation aperture is made which connects the trachea with the outer space, but it is obvious that this measurement has significant disadvantages.

Another known principle for treatment of respiratory insufficiency consists in a certain amount of breathing gas being supplied during the respiratory treatment through a special gas tube to a point in the airway during the latter part of the expiration, the supplied gas volume displacing used breathing gas from the airway above the aforementioned inlet point and the dead space then being decreased. This principle, called airway flushing, is useful but has certain limitations and even in some cases certain disadvantages. Thus, the extra gas supply gives some increase of the airway pressure, which at severe circulation insufficiency can be injurious. Principally, in the case of obstructive airway disease, an abnormal high flow of gas from the alveolus occurs during the entire expiration. Then, if it is attempted to free the airway from used gas by means of airway flushing, the positive effect is partly lost due to the fact that the continuous flow of gas from the alveolus tends to fill again the airway with used gas. A large dilution of the gas flow from the alveolus can be achieved by flushing with a high flow, but then other disadvantages arise, for example further increased airway pressure. Another limitation of the known methods and devices for airway flushing is that they require a respirator and, therefore, cannot be used by patients who are not connected to a respirator.

SUMMARY OF THE INVENTION

It is an object of the present invention to eliminate or at least considerably reduce the aforementioned disadvantages of known methods for reduction of rebreathing of gas from the dead space.

The above object is achieved in accordance with the principles of the present invention in a method and apparatus wherein at least during the final phase of expiration, a flow of used breathing gas is artificially evacuated from the patient through a gas conduit, which is inserted into the patient's airway. The flow rate of the evacuated gas is greater than the flow rate of expiration gas being exhaled by the patient at the time. Breathable gas is simultaneously supplied to the patient through a gas conduit inserted in the airway, which may be the same as is used for evacuation, or may be a separate conduit.

DESCRIPTION OF THE PREFERRED EMBODIMENTS

Figure 1:
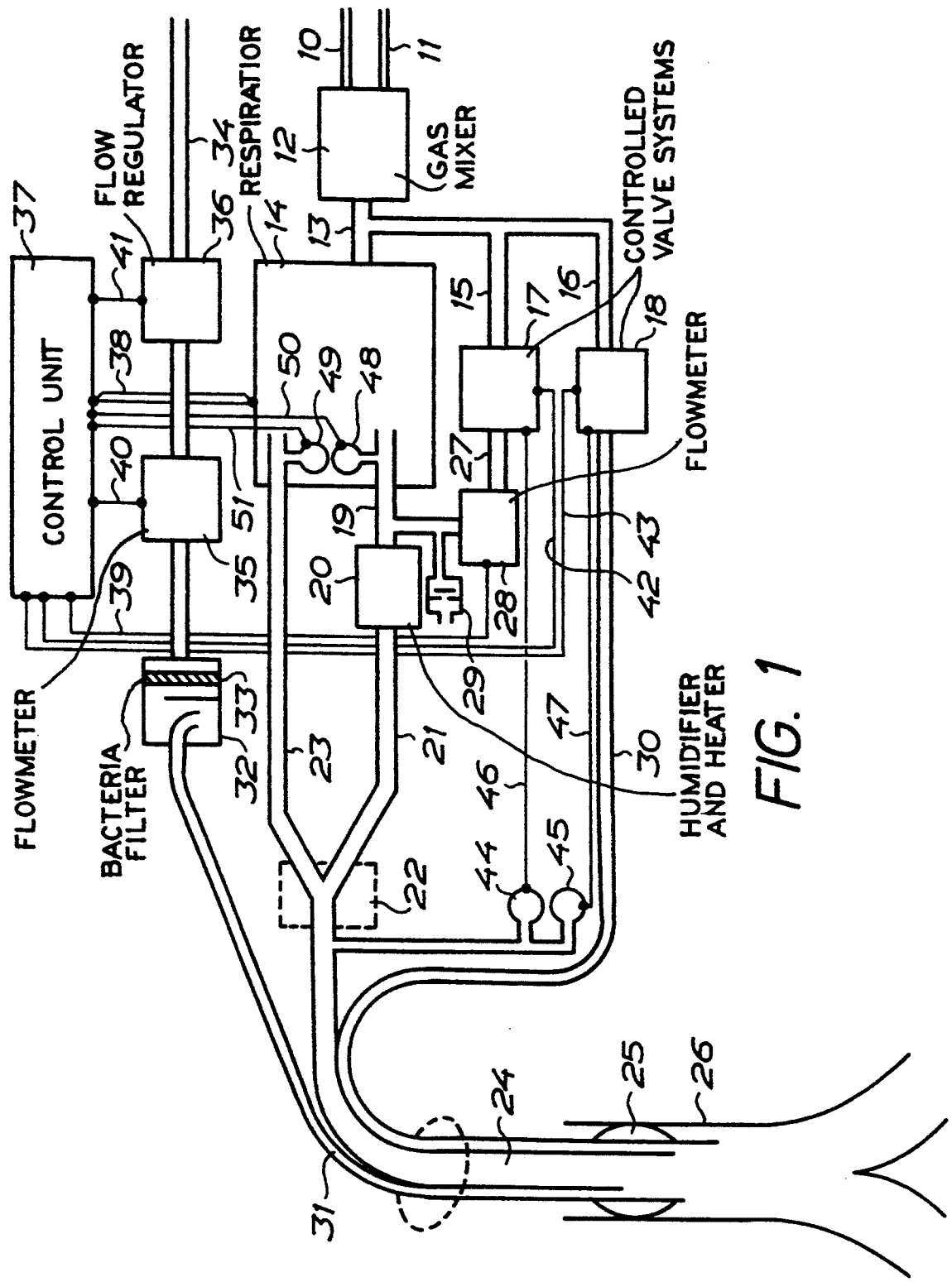
FIG. 1 is a diagram showing an embodiment of a respiration-assist device according to the invention for use in connection with respiratory treatment.

In FIG. 1, two tubes for supply of pressurized breathing gases, are shown, namely a conduit 10 for supply of, for example, air, and a conduit 11 for supply of, for example, oxygen. The conduits are connected to a gas mixer 12 for mixing the gases in desired, adjustable proportions, and from the gas mixer a conduit 13 leads to a respirator 14 which is assumed herein to be a respirator of the type ServoVentilator 900C from Siemens Elema AB, Solna. The conduit 13 is also connected through respective branch conduits 15 and 16 to two electrically controlled valve systems 17 and 18, each comprising a plurality of microvalves of the type LIF LF AA 1200118H from The Lee Company, Westbrook, Conn., USA, which are connected in parallel and are normally closed. The respirator 14 has an outlet conduit 19 for inspiration gas with a humidifier and heater 20 from which an inspiration hose 21 leads to one leg of a Y-tube 22, the other leg of which is connected to the respirator through an expiration hose 23. The Y-tube connects the inspiration and expiration hoses with a tracheal tube 24 which is provided with an inflatable cuff 25 and is intended to be inserted into the patient's trachea which is shown at 26. The tracheal tube can be replaced by a tracheal cannula for connection of the respirator to the patient's airway.

The valve system 17 is connected by a conduit 27 via a flowmeter 28 to the outlet tube 19. The conduit 27 is provided with a mechanical one-way valve 29, which constitutes a safety valve for supply of external air into the inspiration hose 21 if an underpressure should arise in the hose 21, which corresponds to approximately 5 cm $H_2O$. The valve system 18 is connected to a conduit 30 which terminates in an opening close to the opening of the tracheal tube 24. The conduit 30 may consist of a thin catheter which is situated inside the tracheal tube, or can comprise an intramural cavity in the tracheal tube as in the Hi Lo Jet Tracheal Tube from Mallincrodt.

An additional conduit 31 is provided in the same way as the conduit 30 and also terminates with an opening close to the opening of the tracheal tube 24. The conduit 31 is connected through a trap 32 for secretion and a bacteria proof filter 33, combined in one unit, to a conduit 34, which is connected with a vacuum source (not shown) which can consist of a central evacuation system or a vacuum pump. In the conduit 34 there is provided a flow meter 35 and a flow regulator 36, the latter being substantially of the same type as the valves controlling the inspiration and expiration flows of the respirator of the make mentioned herein.

The described device also includes an electronic control unit 37 which may be of the type available from INTEL and which includes, among other things, a microprocessor and an analog-to-digital converter. By a main line 38 the converter is connected to the respirator 14 in order to receive signals therefrom, which indicate respiration phase, flows and pressures in the inspiration and expiration hoses 19, 21 and 23 respectively. The flowmeters 28 and 35 are also connected to the control unit 27 by respective lines 39 and 40, in order to supply to the control unit signals which represent the flow in the conduit 27 and the conduit 34, respectively. A line 41 leads from the control unit to the flow regulator 36 and lines 42 and 43 lead from the control unit to the valve systems 17 and 18, respectively, for the supply of electric signals to these units from the control unit 27 when the microvalves are to be opened. The valve systems 17 and 18 furthermore are respectively connected to pressure sensors 44 and 45 by respective lines 46 and 47.

The respirator 14 includes respective pressure sensors 48 and 49 in the inspiration path formed by conduits 19 and 21 and in the expiration conduit 23. The sensors 48 and 49 are connected to an automatic monitoring system in the respirator to interrupt the expiration at an unsuitable underpressure, for example $-2$ cm $H_2O$, in the expiration circuit and to interrupt the inspiration if an unsuitably high overpressure arises, and these pressure sensors are also connected to the control unit 37 by respective conduits 50 and 51.

By means of the described device, the method of the invention is practiced in the following way:

The respirator 14 operates in the conventional way, wherein gas flows to the patient's breathing system during the inspiration phase through the conduit 19 via the humidifier and the heater 20, and through the inspiration hose 21, the branch piece 22 and the tracheal tube 24, while during the expiration phase used gas is flowing through the tracheal tube and the expiration hose 23. In accordance with known principles, parts of the dead space can be flushed during the latter part of the expiration by one or more valves in the valve system 18 being opened by a signal from the control unit 37 via the line 43, so as to create a constant or pulsating air stream through the gas conduit 30 for the ejection of an airjet close to the opening of the tracheal tube 24. Initially, the gas stream through the expiration hose 23 consists of used gas, but to the extent that used gas does not continue to come from the lungs, parts of the patient's airways as well as the tracheal tube 24, and the Y-piece 22 would become filled with fresh gas from the gas conduit 30, the flushing effectivity thus being reduced.

This disadvantage is eliminated by undertaking in the control unit 37, a comparison of the existing expiration flow with a flow programmed in the control unit 37 so that when the decreasing expiration flow falls below a predetermined value, a signal will be supplied from the control unit 37 via the line 41 to the flow regulator 36, which then will open to such extent that a predetermined flow which is programmed into the control unit 37 will be evacuated from the patient's breathing system through the conduit 31, the trap 32 and filter 33, and the flowmeter 35 and ultimately through the conduit 34, connected to the suction source. This flow should preferably be chosen such that it is of the same order of magnitude as the expiration flow which initiates the above described function. Thus, the flow from the patient's breathing system during the latter part of the expiration phase will be evacuated through the conduit 31, and the corresponding flow through the tracheal tube will cease.

At the same time as the described evacuation is initiated, a signal is supplied from the control unit 37 via the line 42 to the valve system 17 so that the valve system 17, during the expiration phase, will allow a predetermined flow through the conduit 27 via the flowmeter 28 to the outlet conduit 19 of the respirator 14 and via the humidifier and the heater 20 to the inspiration hose 21. As the flow of exhaled gas through the trachea 26 during the continuing expiration phase decreases further in the last part of the expiration phase, the flow will fall below the flow which is being evacuated through the conduit 31, which results in a flow from the inspiration hose 21 through the y-piece 22 and the tracheal tube 24. Fresh heated and humidified gas thus will be supplied to the breathing circuit down to the lower end of the tracheal tube 24 during the last part of the expiration phase. To the extent that the flow of gas thus supplied to the breathing circuit is not considered to be sufficient to flush all of the breathing circuit down to the lower end of the tracheal tube, the flow which is evacuated through the conduit 31 and the flow which is supplied through the conduit 27 via the valve system 17 can be increased to a suitable extent. It has been found that it is suitable to control these two flows in such a way that the flow through the conduit 27 is slightly higher than the flow through the conduit 31, since this provides the advantage that the flow through the expiration hose 23 will be affected to a small extent only. The order of magnitude of this latter flow is of importance inter alia for those monitoring systems which are included in the device in order to check that the patient undergoes sufficient ventilation and the function thereof being described further below. However, at the same time a certain flow is also achieved, which flushes the two legs of the Y-piece 22 and prevents rebreathing, via turbulence, of gas contained in the expiration leg of the Y-piece. Furthermore, the advantage is gained that an end—respiratorical pressure which is adjusted on the respirator 14, will be more easily maintained in the presence of smaller leakage, which may occur mainly in the connection between the tracheal tube 24 and trachea 26 at the sleeve 25.

By practice of the method according to the invention in the device, described with reference to FIG. 1, fresh gas will be brought to fill the airway down to the tip of the tracheal tube 24 during the expiration phase under control by means of the valve system 17 in order to flush the dead space. Further flushing is achieved by the gas jet, which is supplied through the conduit 30 under control by means of the valve system 18, and the gas jet, which in this way is supplied at the opening of the conduit 30 in the lower end of the tracheal tube, will reach down into trachea and the closest branches of airways which then can be flushed. Then preferably the gas flow which is evacuated via the conduit 31 shall be controlled by means of the regulator 36 in such a way that the order of magnitude thereof corresponds substantially to the sum of the flows which are supplied through the valve systems 17 and 18. The adjustment is controlled by means of the control unit 37.

In order to avoid unsuitably high airway pressures from arising in the airway in the event of incorrect handling of the device according to FIG. 1 or a malfunction of this device, the device has several safety systems. The two pressure sensors in the respirator 14 were mentioned above, which are connected to the control unit 37 and interrupt the expiration when an unsuitably high overpressure arises due to more gas being evacuated through the conduit 31 than is supplied by the patient's expiration by causing the valve systems 17 and 18 and the flow-regulator 36 to close by signals from the control unit 37, which are initiated by signals from the pressure sensors 48 and 49 on the lines 50 and 51. If an underpressure should arise as a consequence of an unsuitably adjusted respirator 14 or malfunction thereof, thus interruption acts as a safety function built into the control unit 37, by means of the valve systems 17 and 18 and the flow regulator 36 being closed, in dependence of the signals from the pressure sensors 48 and 49 via the conduits 50 and 51 to the control unit 37, if the pressure sensors indicate a value corresponding to $-4$ cm $H_2O$. The mechanical valve 29 mentioned above starts to function and opens at an underpressure of $-5$ cm $H_2O$, if both pressure sensors 48 and 49 should fail or a fault should arise in the control unit 37.

The pressure sensors 44 and 45 which are respectively connected to the valve system 17 and the valve system 18 by the lines 46 and 47, cause those valve systems to close if the pressure in the tracheal tube 24 should exceed a preadjusted value for the related valve system. This safety function should be such that it is necessary to reset manually for the valve system to open again.

Figure 2:
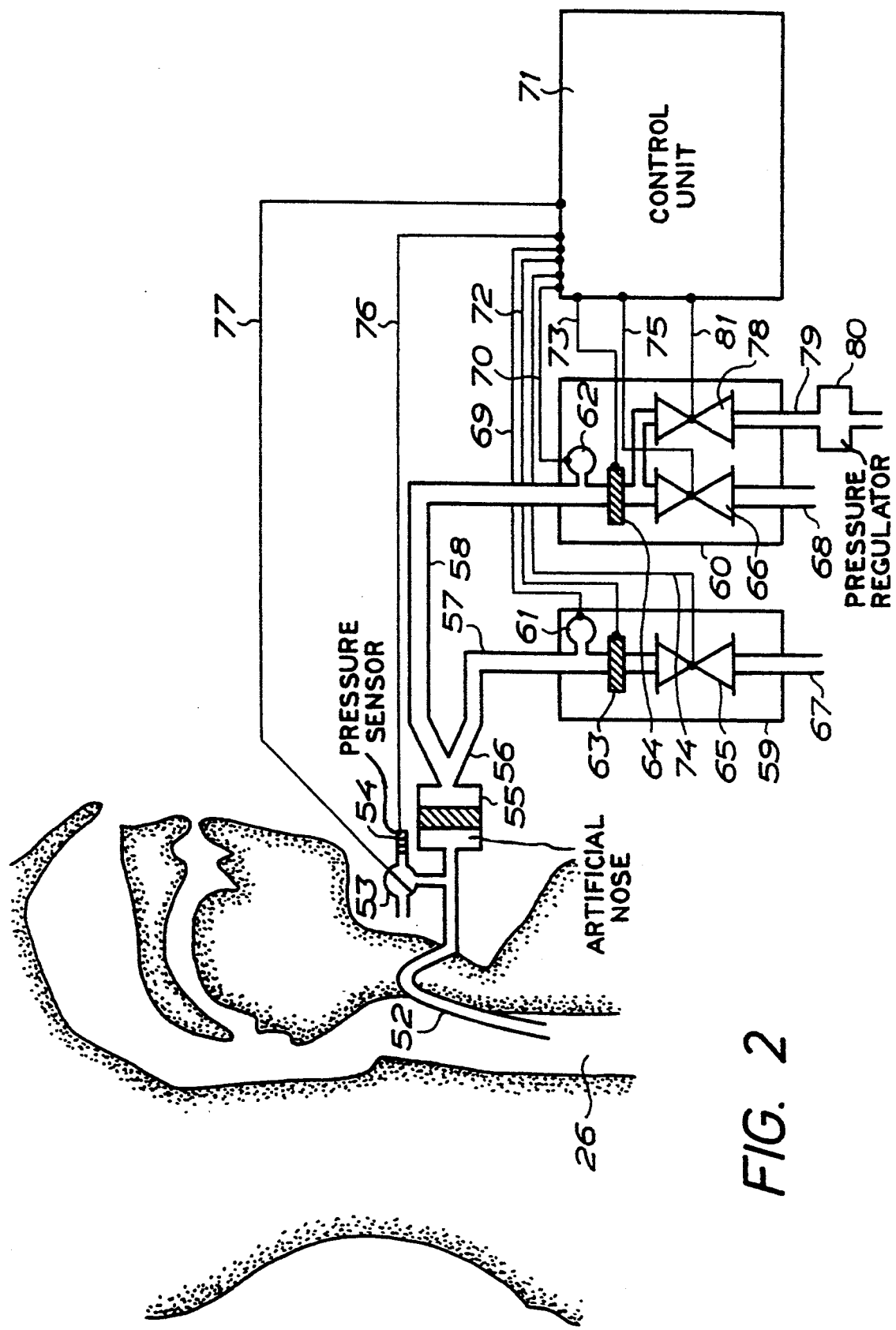
FIG. 2 is a diagram showing an embodiment of a respiration-assist device according to the invention for use during spontaneous breathing.

The embodiment of the device according to the invention which is shown in FIG. 2 is intended to be used by a patient during spontaneous breathing. In this case, a catheter 52 of a subcutaneous type is connected to the trachea 26, but instead a catheter could be inserted through the natural airway and could have the opening thereof in an optional location in the airway, for example in the nasopharynx. To the catheter a two way valve 53 is connected, by means of which a pressure sensor 54 of the type which is used for measuring pressures within body cavities can be connected to measure either the athmospheric pressure or the pressure in the catheter. The catheter is connected to two conduits 57 and 58 via an artificial nose 55, and a branch piece 56, the conduit 57 leading to an evacuation system 59, and the tube 58 leading to a system 60 for gas supply. The artificial nose 55 is constructed according to known principles and comprises a porous hygroscopic material which stores heat and moisture when warm and moist expiration gas passes through the artificial nose to the evacuation system 59, in order to return heat and moisture to the inhaled gas during the inspiration.

The systems 59 and 60 have respective pressure sensors 61 and 62 of the type which is included in the above-mentioned ServoVentilator 900C, and respective flowmeters 63 and 64 also of the same type as in the ServoVentilator 900C. Furthermore, each system 59 and 60 includes a plurality of microvalves connected in parallel of the type LIF LF AA 1200118H from The Lee Company, which have been indicated by respective valve symbols 65 and 66. The evacuation system 59 is connected to a conduit 67 through the valves 65 the conduit 67 leading to a source for underpressure, not shown in FIG. 2, which can comprise, for example, a central system for gas evacuation or an evacuation pump for gases, while the system 60 for gas supply is connected via the valves 66 to a conduit 68 which extends from a source for breathing gas at overpressure, not shown in FIG. 2. The pressure sensors 61 and 62 are connected by respective conduits 69 and 70 to an electronic control unit 71, comprising inter alia an analog-to-digital converter and a microprocessor. The control unit 72 is also connected by respective lines 72 and 73 to the two flow sensors 63 and 64. Via the lines 69, 70, 72 and 73 the control unit 71 receives signals-indicating pressure and flow in the conduits 57 and 58. The control unit 71 is also connected to the valves 65 and 66 by respective lines 74 and 75 to supply signals via these lines, by which a suitable number of the normally closed valves are adjusted to an open position. A line 76 is provided from the pressure sensor 54 to the control unit 71 to supply a pressure signal to the control unit 71 which has a line 77 to the two-way valve 53 for switching that valve between the two adjusted positions thereof, the atmosphere and the catheter, respectively.

Also a conduit 79 is connected to the conduit 58, upstream of the flowmeter 64 through a valve system, indicated in FIG. 2 by a valve symbol 78, of the same type as the valve systems 65 and 66, the conduit 79 being connected via a pressure regulator 80 to a source of oxygen or another gas. The normally closed valves 78 are connected by a line 81 to the control unit 71 in order to open a suitable number of valves on signal from the control unit.

The device according to FIG. 2 operates according to routines which shall be programmed into the control unit 71, according to the example given below.

In an initial phase which according to the program, is repeated at suitable intervals, the pressure sensor 54 will be connected to the atmosphere by a pulse supplied via the line 77 from the control unit 71, switching the two way valve 53. During the period which follows, the control unit 71 will read the signal from the pressure sensor 54, which corresponds to atmospheric pressure. Then, the two way valve 53 will be reset, so that the pressure sensor 54 will be connected to the airway through the catheter 52.

In a second phase the microprocessor, forming part of the control unit 71, reads the signals from all three pressure sensors 54, 61 and 62 during a period corresponding to a number of breaths. The pressure signals 35 are then compared with each other by linear regression. To the extent that the three signals do not show congruity, a fault indication will be given and further functions will be inhibited until the fault has been repaired and manual restart of the system has been made. Normally, the numerical constants which admit direct comparison of the measured pressure signals are stored in the microprocessor.

In a third phase the pressure variation read during the second phase will be analyzed in order to identify the beginning and the end of the inspirations and expirations which have been registered. The lowest pressure measured which is found to be subatmospheric, is identified as an inspiration. The beginning of this inspiration will be searched for and identified as the zero crossing of the pressure which precedes the lowest pressure previously found. If no zero crossing is found during the read period, the beginning of the inspiration is left unidentified. Search for additional pressure minima and preceding zero crossings thereof is made for identification of additional inspirations and their beginning through the entire period which has been read during the second phase. Suitable filters and inhibited (nonenabled) periods are used to eliminate double identification of an inspiration. In the next moment of phase three, pressure maxima between two following inspirations are searched for. It is controlled that the pressure maxima are above the atmospheric pressure and then the maxima are identified as expirations. The beginning of every expiration is identified as the zero crossing of the pressure signal which precedes each pressure maximum. The duration of the inspiration and the expiration is tabulated in the microprocessor together with respective pressure minima and pressure maxima. The process of a typical inspiration and expiration is determined as the final result of the process during phase three, and the typical pressure variation in diagrammatic form as well as numerical information, comprising above all the duration of different phases of the breathing cycle, is presented on a picture screen.

During a fourth phase the registered variation is studied by a therapist, who is assumed to be a doctor or a breathing therapist. This person determines the volumes to be evacuated during the breathing cycle through the conduit 57, and the phase of the breathing cycle during which this is to be made. Furthermore, the therapist determines the volumes to be supplied through the conduit 58 and the phase of the breathing cycle during which this is to be made.

The therapist also adjusts the highest levels concerning underpressure in the catheter 52 during the evacuation phase, and the highest values concerning overpressure in the catheter during gas supply. Limits concerning deviations from the typical breathing pattern, which is studied during phase three, are also determined.

During a fifth phase, which is a therapeutic phase, the device is brought to function in accordance with the principles of the invention and according to the routine established during phase four. During the total therapeutic phase the control unit 71 continuously reads pressure values from the three pressure sensors 54, 61 and 62 as well as flow values from the flowmeters 63 and 64. The digital values are stored in a circulating buffer in the memory of the microprocessor, this circulating buffer having a circulating period which covers several breathing cycles. A subatmospheric pressure minimum is searched for and identified as an inspiration. Then, a superatmospheric pressure maximum is searched for, defining an expiration. When this has been found, the computer searches the beginning of the actual expiration which is identified as the nearest preceding zero crossing of the pressure and is found in the circulating buffer. The processor checks that the time relations between preceding inspiration minimum pressure, the beginning of the actual expiration and the identified maximum pressure thereof correspond to a normal breathing pattern of the patient as established in phase four. If this is the case, the processor sends a signal to the valve system 65 after a period defined during phase four, the valve system 65 passing an evacuation flow which is evacuated through the catheter 52, the artificial nose 55, the conduit 57, the flowmeter 63, the valve system 65 and out through the conduit 67. The rate of the evacuation flow is compared according to known servo-feedback principles with the flow corresponding to the flow required in order that the evacuation volume, determined during phase four, will be evacuated during the determined period. Deviations, if any, will be corrected by connection or disconnection of valves connected in parallel in the valve system 65. In the way described, during the latter part of the expiration, a flow will be evacuated from the airway from the point where the catheter 52 opens. When the flow of gas from the lungs during the expiration decreases and approaches zero, it will at some time fall below the flow of gas which is evacuated through the catheter 52. Then, gas will flow from the opening of the airway, which could be the nose or the mouth depending on the way in which the patient is breathing, down into the airway towards the opening of the catheter 52. The airway will thus be filled from the top thereof with fresh breathing gas during the latter part of the expiration as a consequence of gas from dead space being evacuated from the airway. It should be noted here that a favorable effect of evacuation of used gas exists until during the inspiration the interface between used gas and fresh gas has passed the opening of the catheter 52, to the extent that all used gas above said opening has not already been evacuated during the expiration.

The function during the fifth therapeutic phase can be varied in accordance with the therapeutic program, which has been determined during phase four. When a certain volume of gas has been evacuated during part of the final phase of the expiration, the valves in the system 65 will close in accordance with a program. The control system then checks that a super atmospheric or atmospheric pressure exists in the airway indicating that the inspiration has not started so far, by reading the signal from the pressure sensor 54, which is very quick. During the last part of the expiration, pulses of gas are supplied, according to the regime established during phase four by the control system 71 supplying signals on the line 75 which cause opening of valves in the system 66 under further control of a feedback servosystem, such that the flow, which is measured by the flowmeter 64, corresponds to the determined flow. Alternating with the flow pulses, thus obtained, an evacuation of corresponding volumes of gas takes place by the control system causing valves in the system 65 to open. By this Procedure additional volumes of used gas can be flushed from the airway during the final phase of the expiration.

It is common practice that a catheter 52 of the type shown in FIG. 2 is used by patients having respiratory insufficiency, and that catheters which are inserted through the natural airway are used. The purposes of these catheters is to supply to the patient other breathing gases than air, usually oxygen. The device according to FIG. 2 in this respect offers considerable advantages as compared with known systems for gas supply. It recovers heat and moist from the evacuated gas and returns such heat and moisture to the gas which is then supplied to the patient. This makes complicated devices for heating and humidifying supplied gases unnecessary. An very great advantage is offered by the construction due to the fact that the gas supply can be controlled in such a way that occurs only during an early part of the inspiration, the gas supplied (typically oxygen) in its entirety will be supplied to the alveolar space to increase the oxygenization of the blood. This advantage can be utilized without affecting the above described functions by extra supply of oxygen through the conduit 58. After evacuation and flushing of the airway during the therapeutic fifth phase above, the pressure in the airway is read by the pressure sensor 54. When the pressure has fallen to subatmospheric level, which means that an inspiration has begun, the control unit 71 supplies signals on the line 81, which results in opening of valves in the valve system 78 during extended servo control, such that the intended flow of gas will be supplied to the patient during the intended period, which suitably is limited to the initial part of the inspiration, so that all of the total gas volume supplied without doubt will reach the alveolar space during the inspiration. Then, the control system returns to the task of identifying the following expiration according to the description above.

The device according to FIG. 2 has several built-in safety systems. Control of the function of the conduit system is achieved by measurement of the pressures in the three points where the pressure sensors 54, 61 and 62 are located. The pressure differences are related to the flows measured simultaneously, which permits calculation of the resistance of the catheter 52, the artificial nose 55, and the conduits 57 and 58. These resistances are compared in the control unit 71 with earlier estimated recommended values. Upon deviation from limit values based thereon, the function of the device is interrupted and a warning signal is given. An additional safety test is made in connection with the instantaneous interruption of the flow in the conduits 57 and 58, respectively. The interruption should correspond to a corresponding step response in the pressure measured by the quick pressure sensor 54. If this response is not the expected one, the catheter may have been dislocated and the function of the device will be interrupted. An important safety function is to stop the evacuation of gas if the patient has closed the airway above the point from where gas is evacuated. This causes an abnormally low pressure to be registered by the pressure sensor 62.

Although modifications and changes may be suggested by those skilled in the art, it is the intention of the inventors to embody within the patent warranted hereon all changes and modifications as reasonably and properly come within the scope of their contribution to the art.

We claim:

1. In a respiration-assist system, a method for reducing rebreathing of gas from dead space comprising the steps of:

during a final phase of expiration of a patient, artificially evacuating a flow of used gas from the patient through a first gas conduit inserted into the patient's airway, the flow rate of used gas being evacuated being greater than the flow rate of expiration gas then being exhaled by the patient; and simultaneously supplying a flow of breathable gas to the patient through a second gas conduit inserted into the patient's airway.

2. A method as claimed in claim 1, comprising the additional steps of:

monitoring the flow of expiration gas; and initiating the evacuation of used gas at a predetermined flow of expiration gas.

3. A method as claimed in claim 1 comprising the additional steps of:

monitoring the flow over time of the flow of used gas which has been evacuated to determine an evacuated gas volume of evacuated used gas;

monitoring the flow over time of the flow of breathable gas supplied to the patient to determine a supplied gas volume of breathable gas; and controlling said evacuated gas volume and said supplied gas volume for maintaining said evacuated gas volume and said supplied gas volume in a predetermined relationship.

4. A method as claimed in claim 1 comprising the additional step of:

heating and humidifying said flow of breathable gas before supplying said flow of breathable gas to the patient.

5. In a respiration-assist system incorporating a respirator and an apparatus for reducing rebreathing of gas from dead space, comprising:

a tracheal tube insertable into the airway of a patient, connected to said respirator and supplying breathing gas to and from the patient;

a gas conduit inserted into the patient's airway with said tracheal tube, and receiving expired gas from the patient, the expired gas in said gas conduit constituting used gas;

means for providing an underpressure in said gas conduit;

means for determining a final phase of expiration of said patient;

means for initiating said underpressure in said gas conduit during said final phase of expiration for evacuating said used gas from the patient through said gas conduit; and means for supplying breathable gas from said respirator to the patient through said tracheal tube during said final phase of expiration.

6. An apparatus as claimed in claim 5 wherein said means for determining said final phase of expiration comprises means for measuring a flow of used gas and means for comparing the measured flow of used gas with a predetermined value.

7. An apparatus as claimed in claim 6 wherein said means for measuring a flow of used gas comprises a flowmeter disposed in said gas conduit.

* * * * *